United States Patent
Dobin

(10) Patent No.: US 10,660,539 B2
(45) Date of Patent: *May 26, 2020

(54) METHOD OF USING HUMAN PHYSIOLOGICAL RESPONSES AS INPUTS TO HYDROCARBON MANAGEMENT DECISIONS

(71) Applicant: ExxonMobil Upstream Research Company, Spring, TX (US)

(72) Inventor: Mark W. Dobin, The Woodlands, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 308 days.

This patent is subject to a terminal disclaimer.

(21) Appl. No.: 15/699,465

(22) Filed: Sep. 8, 2017

(65) Prior Publication Data

US 2017/0367611 A1    Dec. 28, 2017

Related U.S. Application Data

(63) Continuation of application No. 13/376,810, filed as application No. PCT/US2010/034563 on May 12, 2010, now Pat. No. 9,788,748.

(60) Provisional application No. 61/238,945, filed on Sep. 1, 2009.

(51) Int. Cl.
| | |
|---|---|
| G01N 33/48 | (2006.01) |
| G01N 33/50 | (2006.01) |
| A61B 5/0484 | (2006.01) |
| G16B 5/00 | (2019.01) |
| G16B 45/00 | (2019.01) |
| G16B 50/00 | (2019.01) |
| A61B 5/0205 | (2006.01) |
| A61B 5/16 | (2006.01) |

(52) U.S. Cl.
CPC ............ *A61B 5/04842* (2013.01); *G16B 5/00* (2019.02); *G16B 45/00* (2019.02); *G16B 50/00* (2019.02); *A61B 5/02055* (2013.01); *A61B 5/165* (2013.01)

(58) Field of Classification Search
None
See application file for complete search history.

(56) References Cited

U.S. PATENT DOCUMENTS

| | | |
|---|---|---|
| 5,247,433 A | 9/1993 | Kitaura et al. |
| 5,555,466 A | 9/1996 | Scribner et al. |
| 5,596,994 A | 1/1997 | Bro |
| 5,762,611 A | 6/1998 | Lewis et al. |
| 6,338,713 B1 | 1/2002 | Chamoun et al. |
| 6,341,267 B1 | 1/2002 | Taub |
| 6,549,879 B1 | 4/2003 | Cullick et al. |
| 7,046,924 B2 | 5/2006 | Miller et al. |
| 7,076,118 B1 | 7/2006 | Westerman |
| 7,162,432 B2 | 1/2007 | Mascarenhas |
| 7,418,116 B2 | 8/2008 | Fedorovskaya et al. |
| 9,788,748 B2 * | 10/2017 | Dobin ............... A61B 5/04842 |
| 2004/0225442 A1 | 11/2004 | Tobias et al. |
| 2005/0116929 A1 * | 6/2005 | Molander ............... G06F 3/013 |
| | | 345/157 |
| 2007/0066916 A1 | 3/2007 | Lemos |
| 2008/0218472 A1 | 9/2008 | Breen et al. |
| 2008/0222670 A1 | 9/2008 | Lee et al. |
| 2008/0255949 A1 | 10/2008 | Genco et al. |
| 2009/0088610 A1 | 4/2009 | Lee et al. |
| 2009/0150330 A1 | 6/2009 | Gobeyn et al. |

FOREIGN PATENT DOCUMENTS

| | | | |
|---|---|---|---|
| JP | 2008059545 A | * | 3/2008 |
| WO | WO 2009/033181 | | 3/2009 |

OTHER PUBLICATIONS

English Machine translation of JP-2008059545-A obtained on Sep. 23, 2019.*
Alvarado, M. et al. (2005) "Improving the Organizational Memory by Recording Decision Marking, Rationale and Team Configuration" *Journal of Petroleum Science and Engineering* 47, 71-88.
Blakeslee, S. (1989) "Earthquake in Northern California", New York Times, Oct. 18, 1989; 1 page. Printed from www.nytimes.com on Apr. 21, 2013.
Diabetes (2010) "The Hutchinson Unabridged Encyclopedia with Atlas and Weather Guide", 3 pages. Retrieved online on Apr. 21, 2013 from www.credoreference.com.
Plate Tectonics (2000), The Dictionary of Physical Geography; 2 pages Retrieved online on Aug. 21, 2013 from http://www.credoreference.com.

* cited by examiner

*Primary Examiner* — Russell S Negin
(74) *Attorney, Agent, or Firm* — ExxonMobil Upstream Research Company—Law Department

(57) ABSTRACT

A method of analyzing hydrocarbon-related data is disclosed. Data representative of a hydrocarbon entity is presented. A physiological response of a viewer of the data is sensed. The physiological response is associated with the data. The data and a representation of the associated physiological response is outputted.

15 Claims, 12 Drawing Sheets

METHOD OF USING HUMAN PHYSIOLOGICAL RESPONSES AS INPUTS TO HYDROCARBON MANAGEMENT DECISIONS

CROSS REFERENCE TO RELATED APPLICATIONS

This Application is a continuation of U.S. patent application Ser. No. 13/376,810 filed Dec. 7, 2011, entitled METHOD OF USING HUMAN PHYSIOLOGICAL RESPONSES AS INPUTS TO HYDROCARBON MANAGEMENT DECISIONS, which was a national stage entry under 35 U.S.C. 371 from PCT/US2010/034563, filed May 12, 2010, entitled METHOD OF USING HUMAN PHYSIOLOGICAL RESPONSES AS INPUTS TO HYDROCARBON MANAGEMENT DECISIONS, which claimed the benefit of U.S. Provisional Application 61/238,945, filed Sep. 1, 2009, entitled METHOD OF USING PHYSIOLOGICAL RESPONSES AS INPUTS TO HYDROCARBON MANAGEMENT DECISIONS. U.S. patent application Ser. No. 13/376,810 and 61/238,945 and international patent application PCT/US2010/034563 are hereby incorporated by reference in their entirety.

TECHNICAL FIELD

Disclosed aspects relate to managing hydrocarbon resources, and more specifically, to using human physiological response as an input to decision-making in identifying and managing hydrocarbon resources.

BACKGROUND OF THE DISCLOSURE

This section is intended to introduce various aspects of the art, which may be associated with aspects of the disclosed techniques and methodologies. This discussion is believed to assist in providing a framework to facilitate a better understanding of particular aspects of the disclosure. Accordingly, this section should be read in this light and not necessarily as an admission of prior art.

In the hydrocarbon industry computer-based or computer-assisted interpretation and decisions are made daily. The interpretation and decisions have associated uncertainty which may not be captured accurately. Attempts to describe the quality and level of certainty (QLOC) associated with these activities to date have focused on either uncertainty associated with data and/or qualitative post-analysis/comments assigned to these data, objects or decisions. Numerous methods are available to represent data uncertainty. These comments, often referred to as metadata, may describe the QLOC for the entire object and may incorporate geologic and data issues. In this process, the human factors associated with interim decisions, poor data, geologic complexity, user bias or lack of experience can be overlooked or not recorded. As a result final decisions may be based on insufficient or erroneous information, resulting in a sub-optimal understanding of the QLOC. There have been efforts to have users document interim issues in a digital journal/diary. This has been found to provide insufficient or erroneous information because user-supplied comments are captured sporadically at best and are subject to user bias, knowledge, and/or experience. Additionally, the comments frequently do not address negativity or lack of confidence in the decision. Furthermore, the comments are not spatially or temporally captured with the object, data or workflow being analyzed. Additionally, this commenting process is time-intensive and therefore is done infrequently, and even when done properly the commenting process increases the time to complete a data evaluation. There is a need in the hydrocarbon industry for time-efficient processes to capture continuous human factors associated with computer based oil and gas interpretation and decisions to improve the quality and level of certainty and understanding within the industry resulting in improved hydrocarbon management.

SUMMARY

In one aspect, a method of analyzing hydrocarbon-related data is provided. Data representative of a hydrocarbon entity is presented. A physiological response of a viewer of the data is sensed. The physiological response is associated with the data. The data and a representation of the associated physiological response is outputted.

According to methodologies and techniques disclosed herein, presenting the data may include displaying the data. The data may be displayed in a graphical form. The representation of the associated physiological response may be displayed in a graphical form, and may be superimposed upon the data. The physiological response may include one or more of: brainwave activity, movement of an eye, position of an eye, gaze, muscle movement, body temperature, heart rate, pulmonary performance, change in tone of voice, a rate of use of an input device, and a position of an input device relative to the presented data representative of the hydrocarbon entity. Outputting the data and the associated representation of the physiological response may include storing the data and the representation in a memory, or displaying the data and a graphical representation of the physiological response. The physiological response may be interpreted based on information regarding the viewer. Outputting the data may include storing the data in a raw form or a processed form.

In another aspect, an apparatus for analyzing hydrocarbon-related data is provided. One or more sensors measure physiological responses of a user viewing hydrocarbon-related data. A processor determines a nature of the physiological response and associates the physiological response with the hydrocarbon-related data responsible therefore. An output mechanism stores information describing the physiological response with the hydrocarbon-related data responsible therefor.

According to methodologies and techniques disclosed herein, the apparatus may further include a display for viewing the hydrocarbon-related data. The output mechanism may be a display or a data storage mechanism. The sensors may include a device that records brainwave activity of the user. The sensors may include an eye-tracking device that senses one or more of eye movement of the user, eye position of the user, and gaze of the user. The eye-tracking device may be mounted on the display. The sensors may sense use of an input device, such as a computer mouse, a computer trackball, or a computer keyboard, as it is manipulated by the user.

In another aspect, a method of hydrocarbon management is provided. Hydrocarbon-related information is obtained. The hydrocarbon-related information is viewed. A physiological response is sensed while the hydrocarbon-related information is being viewed. A representation of the physiological response is presented. Hydrocarbons are managed based on the physiological response.

According to methodologies and techniques described herein, the representation of the physiological response may be presented concurrently with a display of the hydrocarbon-related information. Certainty data related to the hydrocarbon-related information may be obtained, and the certainty data may be presented concurrently with the representation of the physiological response and the display of the hydrocarbon-related information, so that hydrocarbons may be managed based on the certainty data and the physiological response. Sensing a physiological response may include sensing brainwave activity of a user while the user is viewing the hydrocarbon-related information. Sensing a physiological response may include tracking an eye of a user while the user is viewing the hydrocarbon-related information, to determine at least one of eye movement, eye position, and gaze.

BRIEF DESCRIPTION OF THE DRAWINGS

The foregoing and other advantages may become apparent upon reviewing the following detailed description and drawings of non-limiting examples of embodiments.

Figure 1:
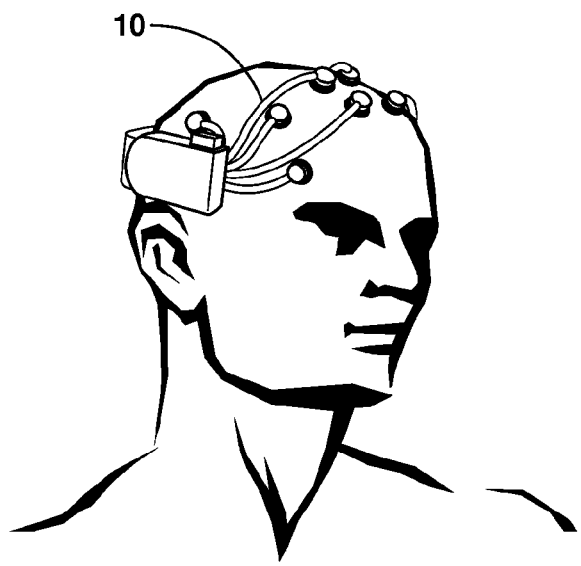
FIG. 1 is a perspective view of a device for measuring brainwave activity.

To the extent the following detailed description is specific to a particular embodiment or a particular use of the disclosed techniques, this is intended to be illustrative only and not to be construed as limiting the scope of the invention. On the contrary, it is intended to cover all alternatives, modifications and equivalents that may be included within the spirit and scope of the invention, as defined by the appended claims.

DETAILED DESCRIPTION

Some portions of the detailed description which follows are presented in terms of procedures, steps, logic blocks, processing and other symbolic representations of operations on data bits within a memory in a computing system or a computing device. These descriptions and representations are the means used by those skilled in the data processing and analysis arts to most effectively convey the substance of their work to others skilled in the art. In this detailed description, a procedure, step, logic block, process, or the like, is conceived to be a self-consistent sequence of steps or instructions leading to a desired result. The steps are those requiring physical manipulations of physical quantities. Usually, although not necessarily, these quantities take the form of electrical, magnetic, or optical signals capable of being stored, transferred, combined, compared, and otherwise manipulated. It has proven convenient at times, principally for reasons of common usage, to refer to these signals as bits, values, elements, symbols, characters, terms, numbers, or the like.

Unless specifically stated otherwise as apparent from the following discussions, terms such as "presenting", "sensing", "associating with", "outputting", "displaying", "superimposing", "storing", "interpreting", "obtaining", "viewing", "managing", "determining", "measuring", "recording", and "tracking", or the like, may refer to the action and processes of a computer system, or other electronic device, that transforms data represented as physical (electronic, magnetic, or optical) quantities within some electrical device's storage into other data similarly represented as physical quantities within the storage, or in transmission or display devices. These and similar terms are to be associated with the appropriate physical quantities and are merely convenient labels applied to these quantities.

Embodiments disclosed herein also relate to an apparatus for performing the operations herein. This apparatus may be specially constructed for the required purposes, or it may comprise a general-purpose computer selectively activated or reconfigured by a computer program or code stored in the computer. Such a computer program or code may be stored or encoded in a computer readable medium or implemented over some type of transmission medium. A computer-readable medium includes any medium or mechanism for storing or transmitting information in a form readable by a machine, such as a computer ('machine' and 'computer' are used synonymously herein). As a non-limiting example, a computer-readable medium may include a computer-readable storage medium (e.g., read only memory ("ROM"), random access memory ("RAM"), magnetic disk storage media, optical storage media, flash memory devices, etc.). A transmission medium may be twisted wire pairs, coaxial cable, optical fiber, or some other suitable transmission medium, for transmitting signals such as electrical, optical, acoustical or other form of propagated signals (e.g., carrier waves, infrared signals, digital signals, etc.).

Furthermore, modules, features, attributes, methodologies, and other aspects can be implemented as software, hardware, firmware or any combination thereof. Wherever a component of the invention is implemented as software, the component can be implemented as a standalone program, as part of a larger program, as a plurality of separate programs, as a statically or dynamically linked library, as a kernel loadable module, as a device driver, and/or in every and any other way known now or in the future to those in the art of computer programming. Additionally, the invention is not limited to implementation in any specific operating system or environment.

Various terms as used herein are defined below. To the extent a term used in a claim is not defined below, it should be given the broadest possible definition persons in the pertinent art have given that term as reflected in at least one printed publication or issued patent.

As used herein, "and/or" placed between a first entity and a second entity means one of (1) the first entity, (2) the second entity, and (3) the first entity and the second entity. Multiple elements listed with "and/or" should be construed in the same fashion, i.e., "one or more" of the elements so conjoined.

As used herein, "computer algorithm" is a set of logical commands that a computer executes.

As used herein, "computer program" is a process that runs inside of the volatile memory of a computer. Computer programs have algorithmic logic and data stored in a binary format. As used in the discussion herein, a computer program does not exist when the computer is dormant and not yet loaded into the volatile memory of a computer. For example, a word processor exists initially on a computer's hard drive as a computer application. When a computer user double-clicks on an on-screen icon representing the word processor, a new computer program is started by compiling and/or executing the computer application associated therewith. When the user exits the word processor the computer program ends. A user can open the word processor twice at the same time, and this would constitute two different running computer programs because each would have its own data and volatile memory assigned thereto. For the purpose of describing aspects of the disclosed techniques, a computer program only exists if all or part of it is executing currently in a computer's volatile memory.

As used herein, "decision-making process" may include one or more of the acts of using a computer to visualize or display information or data, analyzing or interpreting the data or information, and concluding upon a present or future course of action based on the analysis or interpretation.

As used herein, "displaying" includes a direct act that causes displaying, as well as any indirect act that facilitates displaying. Indirect acts include providing software to an end user, maintaining a website through which a user is enabled to affect a display, hyperlinking to such a website, or cooperating or partnering with an entity who performs such direct or indirect acts. Thus, a first party may operate alone or in cooperation with a third party vendor to enable the reference signal to be generated on a display device. The display device may include any device suitable for displaying the reference image, such as without limitation a CRT monitor, a LCD monitor, a plasma device, a flat panel device, or printer. The display device may include a device which has been calibrated through the use of any conventional software intended to be used in evaluating, correcting, and/or improving display results (e.g., a color monitor that has been adjusted using monitor calibration software). Rather than (or in addition to) displaying the reference image on a display device, a method, consistent with the invention, may include providing a reference image to a subject. "Providing a reference image" may include creating or distributing the reference image to the subject by physical, telephonic, or electronic delivery, providing access over a network to the reference, or creating or distributing software to the subject configured to run on the subject's workstation or computer including the reference image. In one example, the providing of the reference image could involve enabling the subject to obtain the reference image in hard copy form via a printer. For example, information, software, and/or instructions could be transmitted (e.g., electronically or physically via a data storage device or hard copy) and/or otherwise made available (e.g., via a network) in order to facilitate the subject using a printer to print a hard copy form of reference image. In such an example, the printer may be a printer which has been calibrated through the use of any conventional software intended to be used in evaluating, correcting, and/or improving printing results (e.g., a color printer that has been adjusted using color correction software).

As used herein, "graphical form" refers to any visual rendering or representation of information or data, such as text or numerical rendering, pictorial rendering, symbology, and the like.

As used herein, "hydrocarbon reservoir" is a reservoir containing any hydrocarbon substance, including for example one or more than one of any of the following: oil (often referred to as petroleum), natural gas, gas condensate, tar and bitumen.

As used herein, "machine-readable medium" refers to a medium that participates in directly or indirectly providing signals, instructions and/or data. A machine-readable medium may take forms, including, but not limited to, non-volatile media (e.g. ROM, disk) and volatile media (RAM). Common forms of a machine-readable medium include, but are not limited to, a floppy disk, a flexible disk, a hard disk, a magnetic tape, other magnetic medium, a CD-ROM, other optical medium, punch cards, paper tape, other physical medium with patterns of holes, a RAM, a ROM, an EPROM, a FLASH-EPROM, or other memory chip or card, a memory stick, and other media from which a computer, a processor or other electronic device can read.

As used herein, "subsurface" means beneath the top surface of any mass of land at any elevation or over a range of elevations, whether above, below or at sea level, and/or beneath the floor surface of any mass of water, whether above, below or at sea level.

As used herein, a "hydrocarbon entity" is any object or workflow relating to hydrocarbon management, and any computer-based interpretation of such an object or workflow. Example objects may include: geologic objects or concepts such as horizons, faults, and intrusive events; stratigraphic features such as unconformities, downlap, offlap, and the like; well trajectories, well casing plans, completion intervals, and hydrocarbon contacts. Other objects may include geologic models, reservoir models, geobodies etc. Workflows may include seismic interpretation, data reconnaissance, well planning, field surveillance, reservoir simulation history matching, geologic interpretation, connectivity analysis etc.

As used herein, "hyrdrocarbon management" includes hydrocarbon extraction/production, hydrocarbon exploration, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities.

As used herein, "gaze" refers to a length of time a user looks at a displayed object or dataset, or at a portion thereof.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional blocks not shown herein. While the figures illustrate various actions occurring serially, it is to be appreciated that various actions could occur in series, substantially in parallel, and/or at substantially different points in time.

Human physiological response (HPR) technology is an emerging technology that has been used in the computer gaming industry, the medical field, and the military to permit a user to interact with a computer. HPR technology as currently deployed, however, uses only a single type of HPR technology in any given application. For example, weapons systems may use an eye-tracking mechanism to identify potential targets. A computer gaming system may detect other physiological responses, such as brainwaves of a computer user, to actively effectuate predetermined instructions or actions in an executing a computer program. According to aspects of the disclosed techniques and methodologies, one or more evidences of human physiological response (HPR) and mechanical attributes are assigned passively and in real-time to hydrocarbon-related data, interpretation of said data, and/or in decision-based hydrocarbon-related workflows. The measurements obtained from one or more HPR sensors may be stored as raw data or as processed data associated with the hydrocarbon-related data, and provide a characterization of the mental state of a viewer of the hydrocarbon-related data.

Types of HPR modalities envisioned include human brainwave responses as detected through electroencephalography (EEG), eye tracking, muscle tracking, cursor movement speeds, digitization rates and the like. Although devices are available to monitor and record single HPR modalities, aspects disclosed herein may combine multiple devices (and modalities) to analyze a given data set. An example of an inexpensive device that monitors a viewer's physiological responses is shown in FIG. 1. Device 10 uses EEG technology and the detection of movement of facial and/or scalp muscles to interpret a viewer's mental state and/or emotion. Device 10 may be a brainwave monitoring headset known as EPOC, supplied by Emotiv Systems of San Francisco, Calif. Conventionally, device 10 may be used to facilitate active human-computer interactions in video/computer games and other computer software. According to disclosed aspects, human physiological responses—such as brain wave activity—are used to passively evaluate, interpret, and otherwise assist making decisions relating to hydrocarbon management. The measurements may be associated with a single input point/event belonging to a hydrocarbon entity. Alternatively, the measurements may be analyzed and assigned to a group of points (subset or local region/area) belonging to a hydrocarbon entity, or may be associated with (or summarized for) the entire hydrocarbon entity. Quality and level of certainty (QLOC) measurements may be visualized to focus a viewer's attention to anomalies in the data, and for various types of data processing activities such as compression, classification, and the like.

Figure 2:
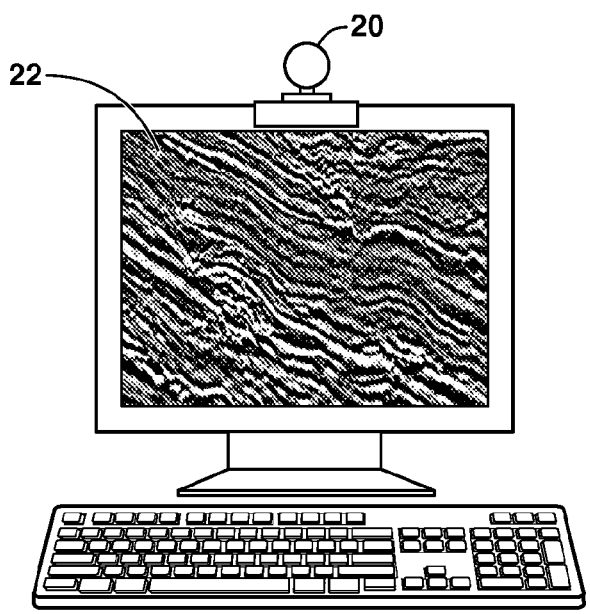
FIG. 2 is a perspective view of a device for measuring eye movement.
Figure 3:
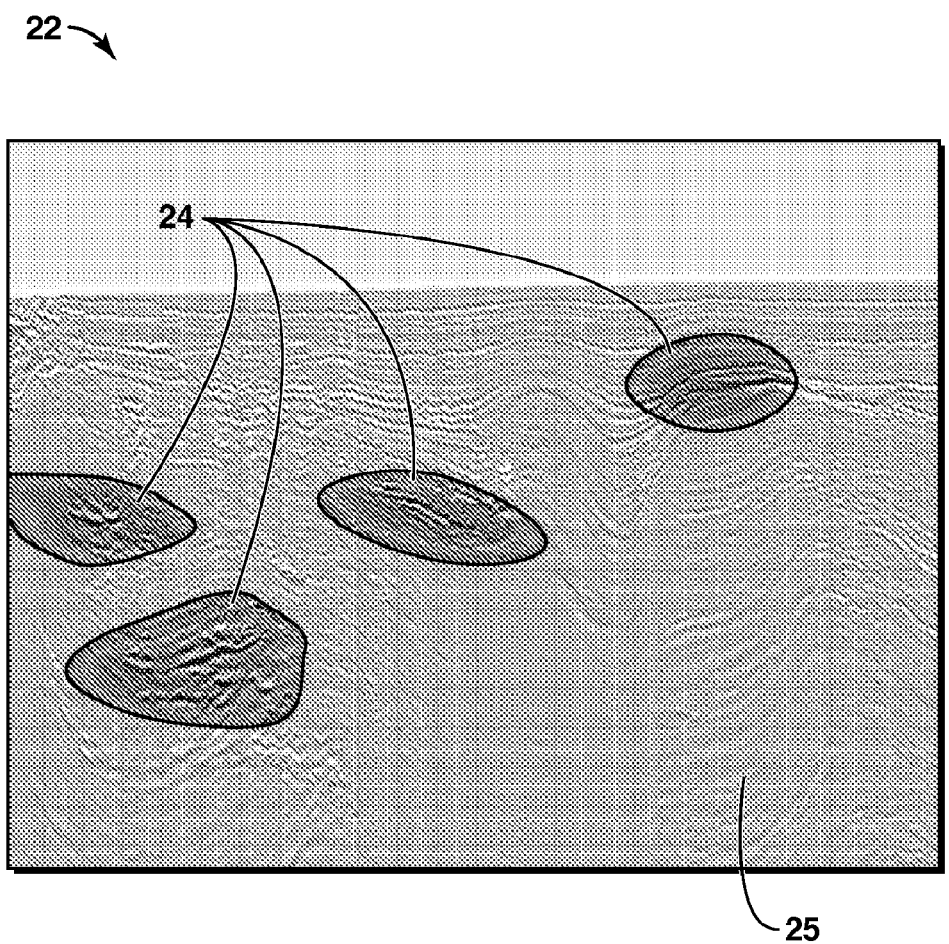
FIG. 3 is a seismic section overlaid with visualization of eye tracking.

Another method of measuring human physiological response is an eye-tracking mechanism, which is shown at reference number 20 in FIG. 2. Eye-tracking mechanism 20 is shown as mounted on a display 22 that is displaying data to be analyzed by a viewer. An alternative eye-tracking mechanism may be mounted on a helmet or other headgear worn by the viewer. The eye-tracking mechanism as discussed herein includes an associated computer program that measures eye movement and position, and can be used to determine precisely what a user is looking at or focusing on. Eye-tracking data obtained by eye-tracking mechanism 20 can be recorded in real-time during a viewer's analysis of displayed data on display 22. The eye-tracking data can be processed and, as shown in FIG. 3 at reference number 24, superimposed on the data (in this case seismic data 25) that is displayed on display 22. The processing of eye-tracking data may vary from a simple summing of eye-tracking events to a more complex process that would involve automated identification of data regions where anomalous eye-tracking activity is detected.

Still another method of measuring human physiological response is through the tracking of muscle movement and/or other physiological mechanical activities the user performs while interacting with the computer. One example of this is merely noting the keystrokes or mouse clicks performed by a user while evaluating a displayed geologic data set. For example, the rate at which a user clicks a mouse while evaluating a data set may be related to the amount of time the user is focusing on a particular displayed data set. A low mouse click rate suggests more time is being taken to evaluate the data set, while a high mouse click rate suggests less time is being taken to evaluate the data set. The mouse click rate may be compared against an average mouse click rate of the specific user evaluating the data set to determine whether the time the specific user is taking to view a data set is greater or less than normal for that user. Another method of measuring mechanical HPR input may include tracking actual cursor position.

In addition to brainwaves, eye tracking and mechanical computer interactions, other HPR modalities that may be measured and recorded are: non-brain-related electrical signals, such as heart rate; external or internal body temperature changes, which may indicate stress or excitement; and pulmonary performance, such as breathing rate or breathing depth.

It is to be understood that any apparatus, system, or device for measuring human physiological response may include a hardware component (such as device 10 or eye-tracking mechanism 20) as well as a computer software component that processes signals from its respective hardware component, as will be further described below.

Figure 4:
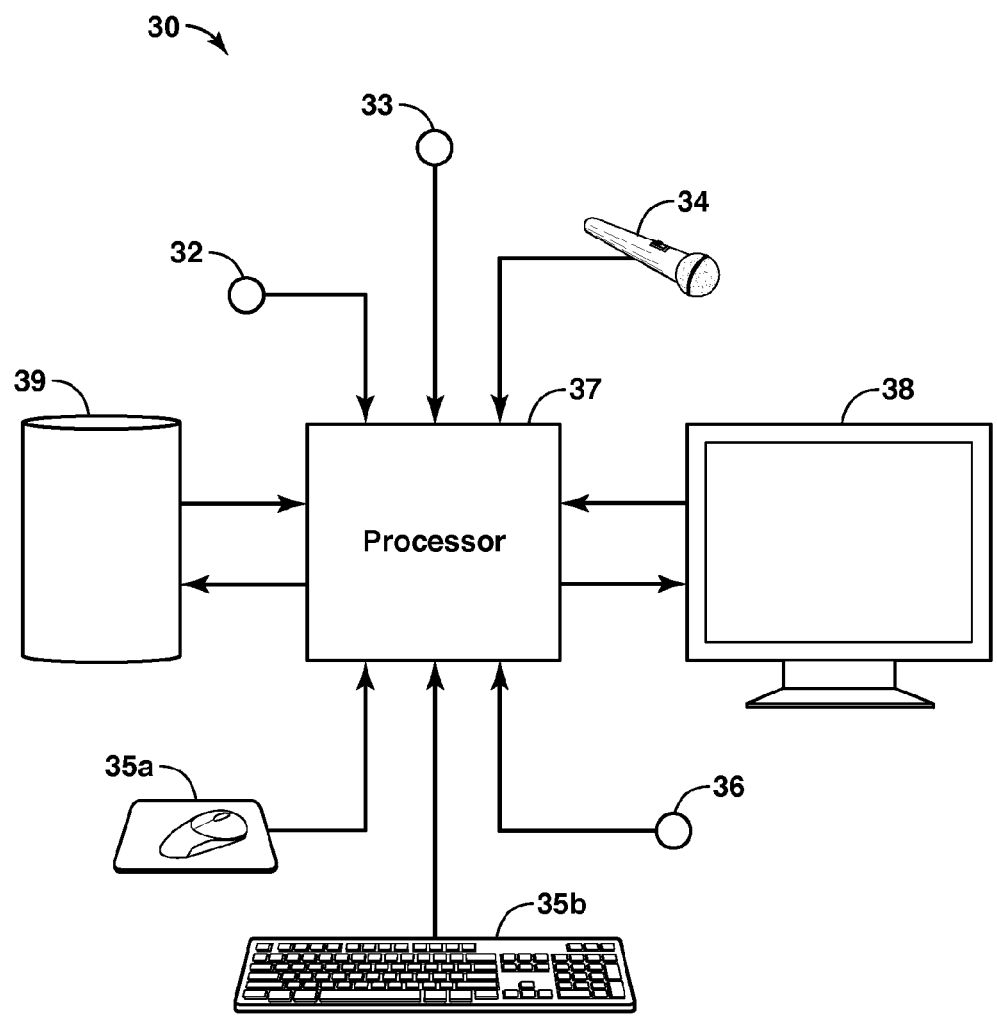
FIG. 4 is a block diagram of a system using human physiological response information. This system could consist of 1 or more human physiological response (HPR) monitoring devices.

The HPR modalities disclosed herein may be used separately or in combination. FIG. 4 shows a simplified diagram of a system 30 using multiple HPR modalities according to aspects of the disclosed methodologies and techniques. System 30 includes a device 32 to measure brainwave activity and facial/scalp muscle movement. Device 32 may be similar to device 10 in FIG. 1, which uses EEG technology or other means to measure brainwave activity and facial/scalp muscle movement. System 30 also includes an eye-tracking mechanism 33 that determines what a user is looking at or focusing on. Eye-tracking mechanism 33 may be similar to eye-tracking mechanism 20. A microphone 34 may be used to record oral commentary as well as to sense stress levels detectable in the user's voice. A mouse 35a and/or keyboard 35*b* provides mechanical input as previously described. Other HPR sensors 36, such as heart rate, temperature, blood pressure, may be part of system 30. The device 32, eye-tracking mechanism 33, microphone 34, mouse and/or keyboard 35*a*, 35*b*, and other HPR sensors send signals to a processor 37 in response to a user viewing a visual representation of a dataset on a display 38. The eye-tracking mechanism determines which portion of the displayed data set is being focused on by the user. Device 32 senses brainwave activity and/or facial muscle movement, and the other HPR sensors record the user's reaction to the focused-on portion of the displayed dataset. Any computer software component of an HPR apparatus, system, or device may be run on processor 37. The processor includes further capability, through additional computer software installed thereon, to analyze the sensed reaction of the user for a given portion of the displayed dataset. For example, brain wave activity indicating a confused or unsure mental state suggests that whatever is being looked at or focused on by the user may need further review. Brain wave activity indicating a happy or excited state may suggest that whatever is being looked at or focused on indicates positive results and/or certainty in the dataset. The system may modify the displayed dataset by graphically or visually highlighting or outlining the focused-on regions. The system may store the modified dataset in a memory or other data storage device 39. Alternatively, the sensed HPR information may be stored in a raw or unprocessed state for further analysis, examples of which may be described below.

Figure 5:
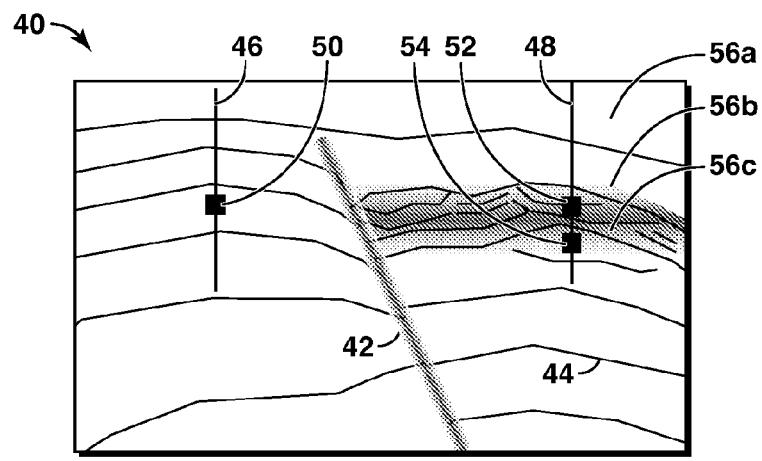
FIG. 5 is a side elevational view of a two-dimensional seismic section showing primary reflectors along with 2 wells.
Figure 6:
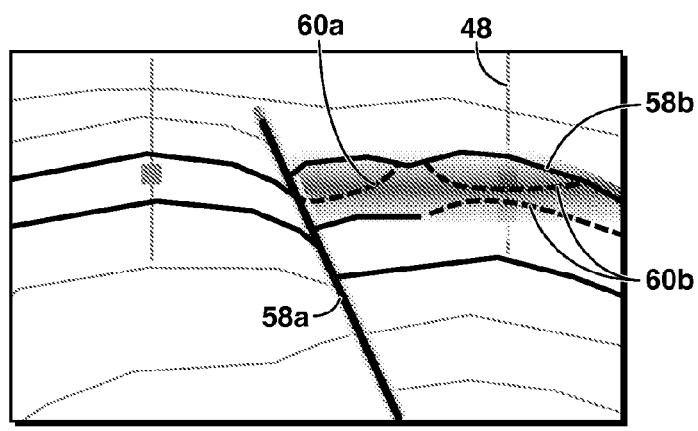
FIG. 6 is a side elevational view of the two-dimensional seismic section of FIG. 5 as interpreted by a geoscientist.
Figure 7:
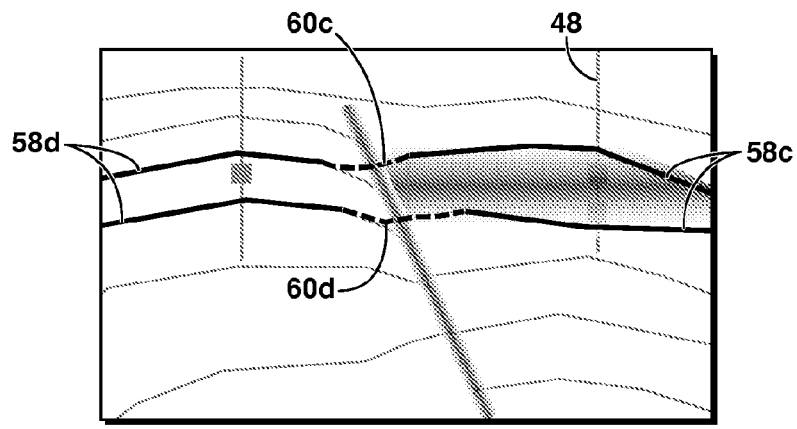
FIG. 7 is a side elevational view of the two-dimensional seismic section of FIG. 5 as interpreted by a non-geoscientist.

The use of HPR technologies may be used with other data uncertainty measures as well as incorporating information regarding the viewer. Recording viewer information aids in correctly interpreting the significance of the HPR responses. FIGS. 5-7 depict an example of how recording viewer information aids such a correct interpretation. An example is the task of creating a seismic interpretation between two wells to determine whether an infill well is required to be drilled. FIG. 5 depicts a two-dimensional seismic section 40 showing primary features that have reflected the seismic signals, such as a fault 42 and a stratigraphic boundary 44, along with two wells 46, 48. Black rectangles 50, 52, 54 represent completion intervals where the wells have encountered hydrocarbons. Uncertainty associated with the seismic data is shown by three distinct shades of gray 56*a*, 56*b*, 56*c*. When the seismic section is viewed by a geoscientist, the geologic and geophysical and reservoir experience of the geoscientist provides valuable contextual information on how to interpret the seismic data. As shown in FIG. 6, solid lines 58*a*, 58*b* superimposed on the seismic data represent high confidence in certain geologic formations, and superimposed dashed lines 60*a*, 60*b* represent low confidence in other geologic formations. In contrast, a non-geoscientist viewing the seismic data will form different conclusions, as shown in FIG. 7 by superimposed high-confidence lines 58*c*, 58*d* and low confidence lines 60*c*, 60*d*. In particular, comparing the confidence levels shows the geoscientist has low confidence about the geologic structure around well 48 (FIG. 6) while the non-geoscientist has high confidence about the same features (FIG. 7). This high confidence is attributed to the non-geoscientist's lack of geologic and engineering experience. For this example, the geoscientist's interpretation is correct. The lack of confidence of the geoscientist highlights areas of difficult interpretation due to poor data quality, complex geology, and reservoir information. The HPR information displayed by the geoscientist's interpretation may be valuable information for future work and may help identify areas that are more uncertain and may require additional review.

The example shown in FIGS. 5-7 demonstrates that the significance/meaning of HPR events can be further enhanced by incorporating the experience and knowledge of a viewer of a dataset. User information may be stored in a user profile and accessed whenever the user is reviewing datasets. A user profile may contain information such as years of service, areas of expertise (geology, geophysics, reservoir engineering, etc.), work experience (exploration, development, production), geologic experience (elastics, deep water, carbonates, overthrust etc.), engineering experience (drilling, simulation, operations, etc.), and other information relevant to analyzing data sets. Incorporating the user information into dataset analysis may provide additional context as to the mental state of a viewer of a dataset. The user profile can be either entered manually into a system that manages the HPR, or the user profile can be obtained from a user's computer login name. The user profile can then be modified manually by the user. Alternatively, the user profile may be modified with statistics from previous HPR responses stored in the HPR management system. For example, the user profile may be automatically re-evaluated based on the user's HPR responses, or even based on other users' HPR responses.

Aspects described herein increase the overall understanding of the certainty associated with interpretation and decision-making workflows in hydrocarbon management, improve the quality of interpretation, and reduce time to adopt new interpretation scenarios by identifying areas which could have multiple options or low QLOC. The potential business impact is improved reservoir management and ultimately increased profits.

Aspects of the disclosed methodologies and techniques may aid in hydrocarbon management in many ways. For example, a user may interpret subterranean or subsurface geologic features of interest using a multi-modality system as shown in FIG. 1 or FIG. 4. The user activates the HPR system and begins the subsurface seismic interpretation process. The HPR system begins recording, noting the user's name. While the user is interpreting a subterranean surface the HPR system records and stores the HPR signals, and associates the HPR signals with the subterranean surface and/or each of the surface's individual components (seismic, horizons, faults, wells etc) as displayed on a monitor. The HPR signals may be associated with data elements of any size (for example, points, lines, sets of points, geometric/geographic objects, surfaces, volumes, entire dataset). The HPR data may be visualized during the interpretation process or after the initial interpretation is completed. HPR data may be incorporated with information regarding data uncertainty to further develop a more holistic understanding of uncertainties involved in the interpretation activity. HPR information may help identify the presence of subtle features (such as small faults, stratigraphy, hydrocarbon indicators, etc.) while interpreting by showing areas on the interpreted surface where, even though the feature wasn't interpreted because the user was thinking about the feature possibly existing, it would be identified by HPR inputs and shown on the final interpretation. This type of analysis and visualization could occur either during or after the interpretation of the surface.

Figure 8:
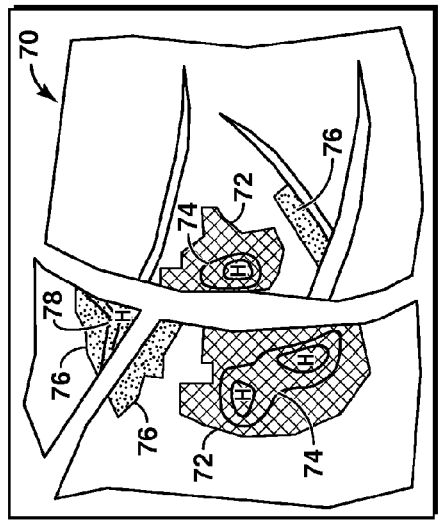
FIG. 8 is a map view of a geologic dataset with confidence levels, derived from HPR inputs, graphically displayed thereon.

Another post-interpretation use of HPR is to assess the quality of a HPR-assisted interpretation. In this example, combining the HPR modalities with conventional data uncertainty techniques could provide insights into the level of certainty of the HPR-assisted interpretation. Assessing this level of certainty may be helpful when making hydrocarbon management decisions such as well placement, well design, platform placement, reservoir management etc. FIGS. 8-12 demonstrate how HPR-assisted dataset interpretation can be combined with data uncertainty analysis to decide where to locate a well. FIG. 8 is a graphical display 70 of a dataset representing a subsurface region of interest as viewed from above. A viewer, wearing a brainwave-sensing device such as device 10 in FIG. 1, views the graphical display while the viewer's EEG signals are detected by device 10 and recorded. Signals sensed by device 10 may indicate the viewer is highly confident of certain portions of the dataset. These high-confidence areas may be superimposed on the graphical display and are shown as gridded areas 72. The high-confidence areas may be further ranked, such as by contouring 74, with the points of highest confidence being indicated by the letter "H", for example. On the other hand, signals sensed by device 10 may indicate the viewer is highly confused by certain other portions of the dataset. These high-confusion areas may be superimposed on the graphical display and are shown as stippled areas 76. The high-confusion areas may be further ranked, such as by contouring 78, with the points of highest confusion being indicated by the letter "H", for example. Other mental states, such as thinking, stress, and others, may be sensed and superimposed on the graphical display.

Figure 9:
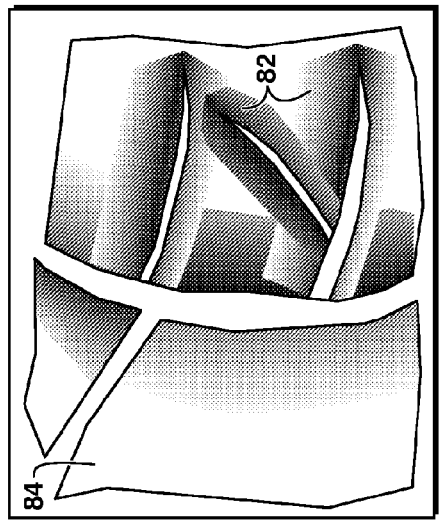
FIG. 9 is a map view of the geologic dataset of FIG. 8 with data uncertainty graphically displayed thereon.

The user may also be employing an eye-tracking mechanism as described herein and shown in previous Figures. FIG. 9 shows areas of the graphical display that were gazed on by the user, as sensed by the eye-tracking mechanism, with darker areas 82 indicating a longer gaze and lighter areas 84 indicating a shorter gaze.

Figure 10:
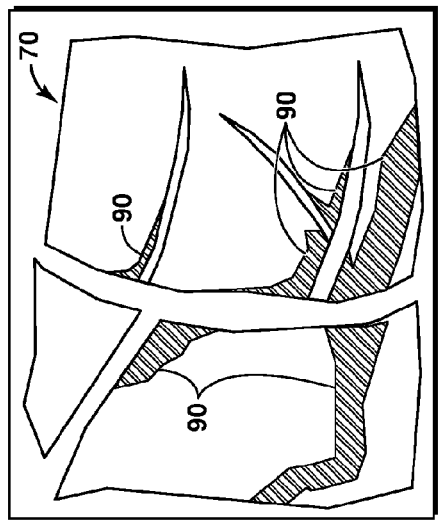
FIG. 10 is a map view of the geologic dataset of FIG. 8 with eye tracking results, derived from HPR inputs, graphically displayed thereon.

The dataset displayed by graphical display 70 may have a measure of uncertainty associated therewith. Such uncertainty may be due to potential errors in gathering the dataset, analyzing the dataset, or other events or acts that may affect the quality and/or uncertainty of the dataset. FIG. 10 depicts a single level of uncertainty superimposed on portions 90 of the graphical display 70 of the dataset, although many uncertainty levels may be calculated and/or displayed if desired.

Figure 11:
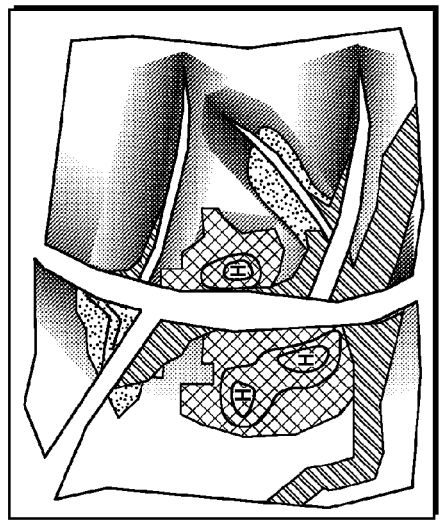
FIG. 11 is a map view of the geologic dataset of FIG. 8, with the information of FIGS. 8 and 9 also displayed thereon.
Figure 12:
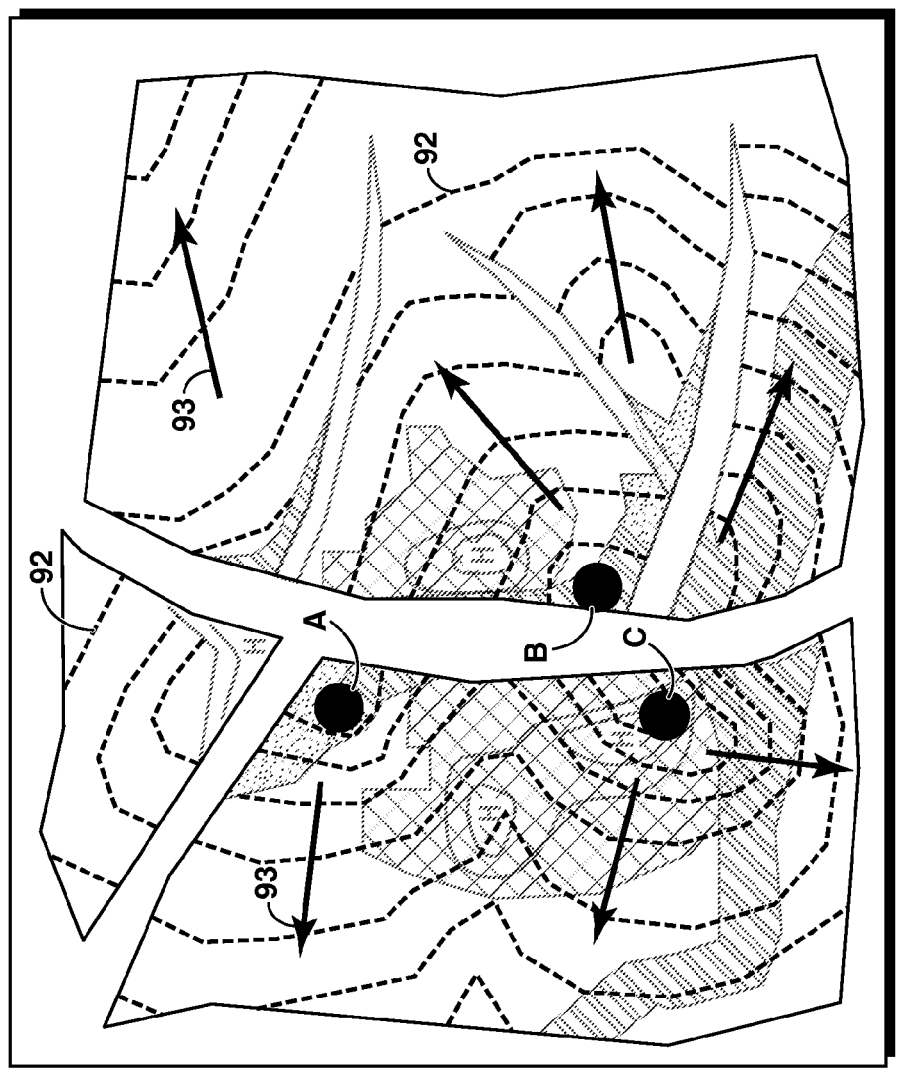
FIG. 12 is a map view of the geologic dataset of FIG. 11 with structural contours displayed over the HPR information.

FIG. 11 shows how the results from HPR sensors (FIGS. 8 and 9) and uncertainty analysis (FIG. 10) may be superimposed simultaneously on the graphical display of the dataset to create a more holistic or complete representation of how the viewer has analyzed the dataset. An additional set of information about the dataset is shown in FIG. 12, in which structural contour lines 92 are superimposed on the graphical display. Arrows 93 point in directions of decreasing structural elevation. All the information superimposed on the graphical display may assist in deciding on potential site for a well. Three candidate sites, A, B, C, are shown in FIG. 12. Candidate site A is located at a high elevation point, but this location was marked as a highly confusing site by the user (FIG. 8). Additionally, candidate site A was marked as a site characterized by data uncertainty (FIG. 10). Candidate site B is located at a high elevation point, but this location was marked as a site characterized by data uncertainty (FIG. 10). Furthermore, while candidate site B is not an area of high confusion or high confidence (FIG. 8), it was virtually ignored by the user (FIG. 9). Candidate site C, on the other hand, is located in an area of high confidence (FIG. 8), and is not located in an area of data uncertainty (FIG. 10). Based on the combined inputs as visually expressed in FIGS. 8-12, candidate site C is the preferred well location.

In another aspect, it may be desired to examine a previous interpretation or decision for quality control purposes or other purposes. If the interpretation/decision has HPR attributes associated therewith, the user may use the existing HPR responses to robustly identify and review regions and features that when initially interpreted had anomalous QLOC measurements. In such a review mode these potentially anomalous features are presented automatically to the user, thereby making the review of QLOC a guided process. The HPR measurements of the reviewing user may be added to the existing interpretation or decision object, thereby providing an additional set of information to the dataset. On the other hand, if the interpretation/decision does not have HPR attributes associated therewith, the HPR attributes of the reviewing user are sensed while evaluating the previous interpretation or decision. The HPR attributes of the reviewing user are collected and associated with the events and objects as they are reviewed. In addition, other information relating to editing/manipulation of the object (such as time of review, duration of review, and the identity of the reviewing user) could be associated with the object to provide additional information relating to the interpretation of the object.

In another aspect, it may be possible to evaluate certainty in recently collected data (or analogous predictions) associated with reservoir and/or well performance. Such data may include produced/injected volumes, well tests, production/profile logs, pressure measurements, and/or seismic data. While conducting this certainty evaluation, a user is wearing a device that senses brainwave activity or other human physiological responses. The physiological responses are then associated with the corresponding data (or analogous predictions) as new attributes indicating certainty. These attributes could then be queried and visualized to make decisions at the field scale (such as collecting additional data or conducting further analysis) and to share insights with other team members, new staff, management, field personnel, etc. HPR measurements such as those measuring brainwave activity may be tracked over time to evaluate individual performance or to determine benefits from training, a user's ability to assimilate new responsibilities, and to evaluate changes in certainty with changes in practices used to collect data and/or generate predictions.

In another aspect, a human physiological response may be associated with data or interpretation/decision objects. While a user is examining data an HPR recording device may record HPR attributes such as brainwave activity, gaze, cursor position, rate of actuating an input device such as a mouse, etc. The HPR attributes are associated with the raw data or interpretation objects. The recorded attributes can be used to determine what data the user considered when reviewing the given dataset. For example, a hyrdocarbon asset such as a well or reservoir may be considered for abandonment. Reviewing the memory attributes associated with a dataset representing the hydrocarbon asset may aid in identifying areas which weren't originally considered during the initial interpretation/decision making process. This process could be further specialized by identifying specific types of objects for which the attributes will be recorded.

Figure 13:
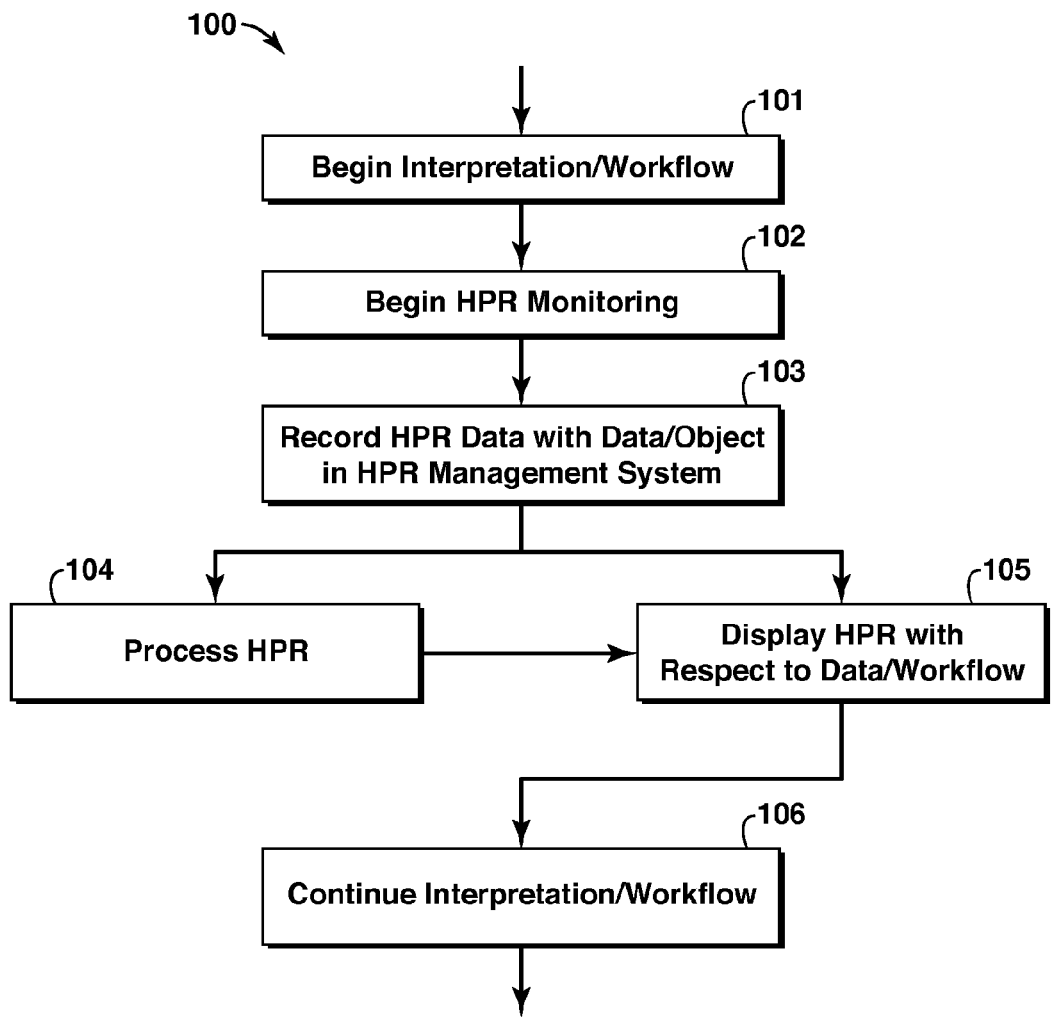
FIG. 13 is a flowchart of a method using HPR techniques in a hydrocarbon management decision workflow.

FIG. 13 is a flowchart showing a method 100 according to aspects of disclosed methodologies and techniques. According to the method, at block 101 a computer-based data interpretation or decision-making work flow is initiated. Example workflows include seismic interpretation, well planning, geologic interpretation, well design, history matching, reservoir surveillance, or other computer-based decision-making process related to hydrocarbon management. A user is wearing or accessing an HPR monitoring device such as the headset of FIG. 1, the eye-tracking mechanism of FIG. 2, and/or a muscle-movement or mechanical event tracking mechanism such as a computer mouse or trackball, or the like. At block 102 the monitoring of human physiological responses commences while the user is reviewing the data or workflow. At block 103 human physiological responses are recorded, associated with the interpretation and/or analysis of data or workflow, and stored in the HPR management system either in raw form or in a processed form. At block 104 the HPR data is retrieved from the HPR management system and then processed separately, in any combination with other human physiological responses, and/or with data uncertainties with the output. The processed data is then stored in the HPR management system as a new attribute associated with the portion of the data or workflow that caused the human physiological responses. At block 105 the results of block 103 and/or block 104 are displayed or otherwise visualized to better understand the QLOC. At block 106 the data interpretation/workflow is continued, taking into account the results of block 103 and/or block 104. This visualization may be on a display with or without the data or workflow with which the processed HPR data is associated.

Figure 14:
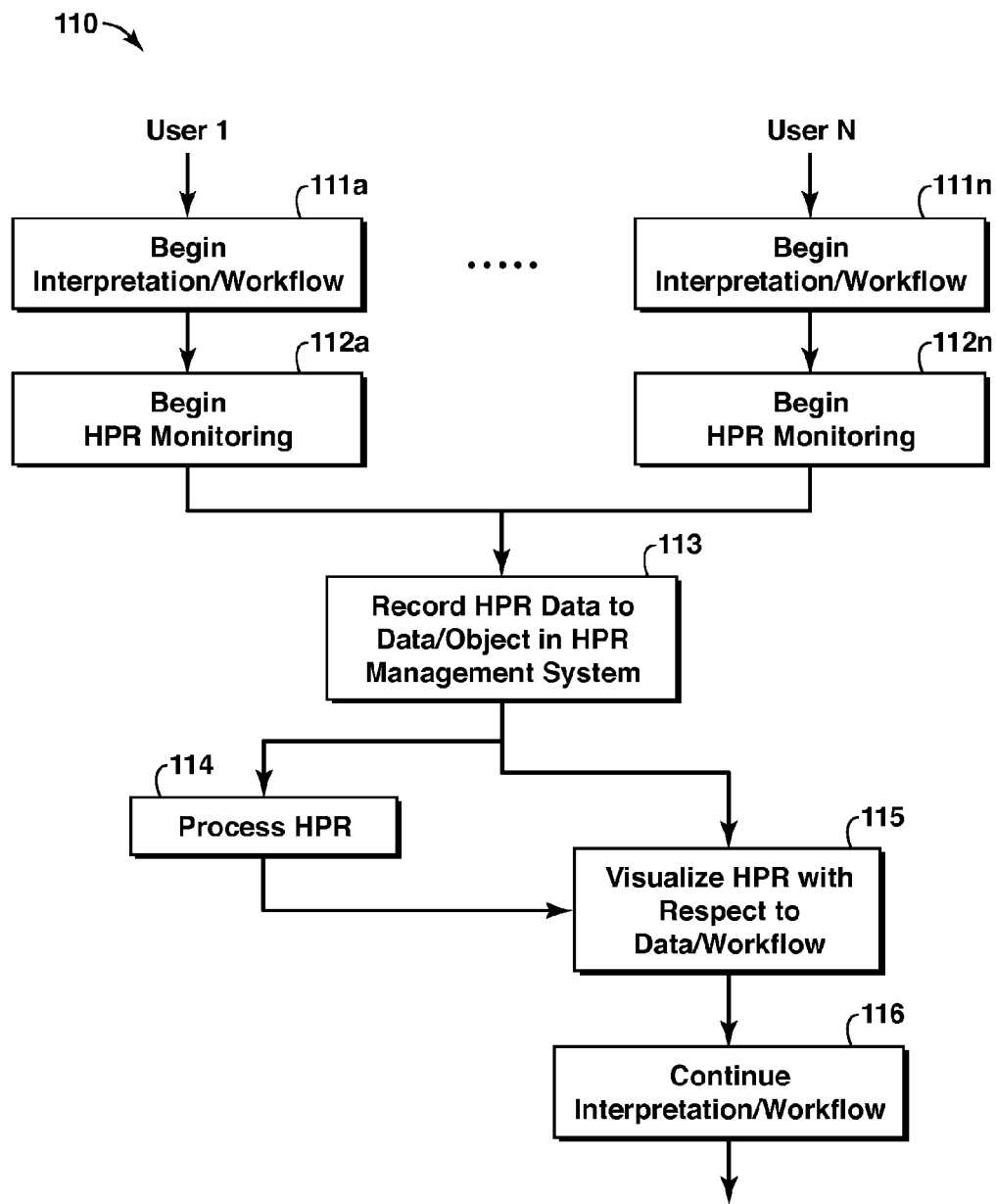
FIG. 14 is a flowchart of a multi-user method using HPR techniques in a hydrocarbon management decision workflow.

FIG. 14 is a flowchart showing a method 110 according to another aspect of the disclosed methodologies and techniques in which multiple users are interpreting data or evaluating workflows using human physiological response technology. For the sake of brevity blocks in FIG. 14 similar to blocks in FIG. 13 are not fully described again, it being understood that the description of FIG. 13 applies to FIG. 14. At blocks 111a . . . 111n each user begins a computer-based data interpretation or decision-making work flow. Such interpretation is not required to be at the same time. The interpretations can be weighted equally or weighted according to relative experience or qualifications. The interpretations may be weighted by other factors as well. One interpretation can be a check or review of another interpretation. At blocks 112a . . . 112n the monitoring of human physiological responses events commences. At block 113 human physiological responses are recorded, associated with the interpretation and/or analysis of data or workflow, and stored in the HPR management system either in raw form or in a processed form. At block 114 the HPR data is retrieved from the HPR management system, processed, and stored in the HPR management system as a new attribute associated with the portion of the data or workflow that caused the physiological responses. At block 115 the results of block 113 and/or block 114 are displayed or otherwise visualized to better understand the QLOC. At block 116 the data interpretation/workflow is continued, taking into account the results of block 113 and/or block 114.

Figure 15:
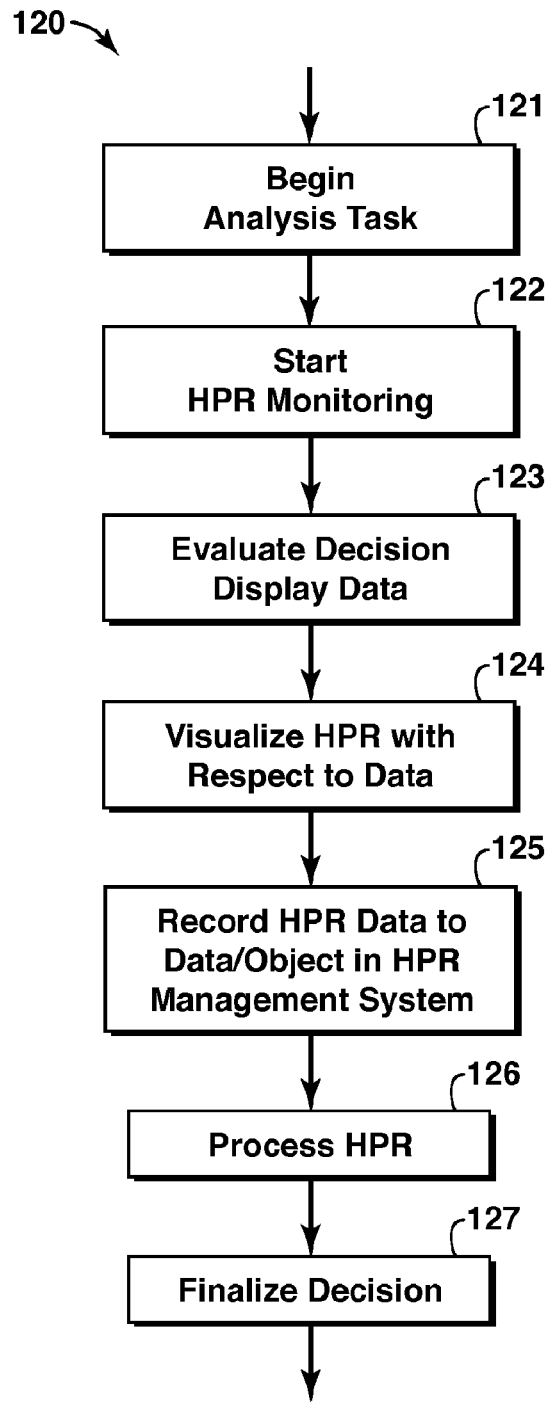
FIG. 15 is a flowchart of a method using HPR techniques in a hydrocarbon management decision workflow according to another aspect.

FIG. 15 is a flowchart showing a method 120 according to another aspect of the disclosed methodologies and techniques. Method 120 demonstrates how HPR technologies may be used to evaluate previous data interpretations/decisions or workflow results. At block 121 the analysis task is begun. At block 122 human physiological responses are monitored, as previously described with respect to blocks 102 and 112 of previously described aspects. At block 123 data relating to a previously made decision is displayed and evaluated while HPR technologies are being employed. At block 124 data representing human physiological responses is displayed or otherwise visualized with respect to the previously-analyzed data. This displaying of HPR data may be accomplished by superimposing numeric or graphic elements representing the HPR data (as shown in FIGS. 3 and 5-12, for example) onto the previously analyzed data. At block 125 physiological responses events are recorded, associated with the interpretation and/or analysis of data or workflow, and stored in the HPR management system either in raw form or in a processed form. At block 126 the HPR data is retrieved from the HPR management system and then processed separately, in any combination with other physiological responses, and/or with data uncertainties with the output. The processed data is then stored in the HPR management system as a new attribute associated with the portion of the data or workflow that caused the physiological responses. at block 127 the processed HPR data is then used to finalize a decision relating to the previous data interpretation and/or workflow. Alternatively, the processed HPR data may be used to evaluate an initial decision made without integrating HPR data therewith.

Figure 16:
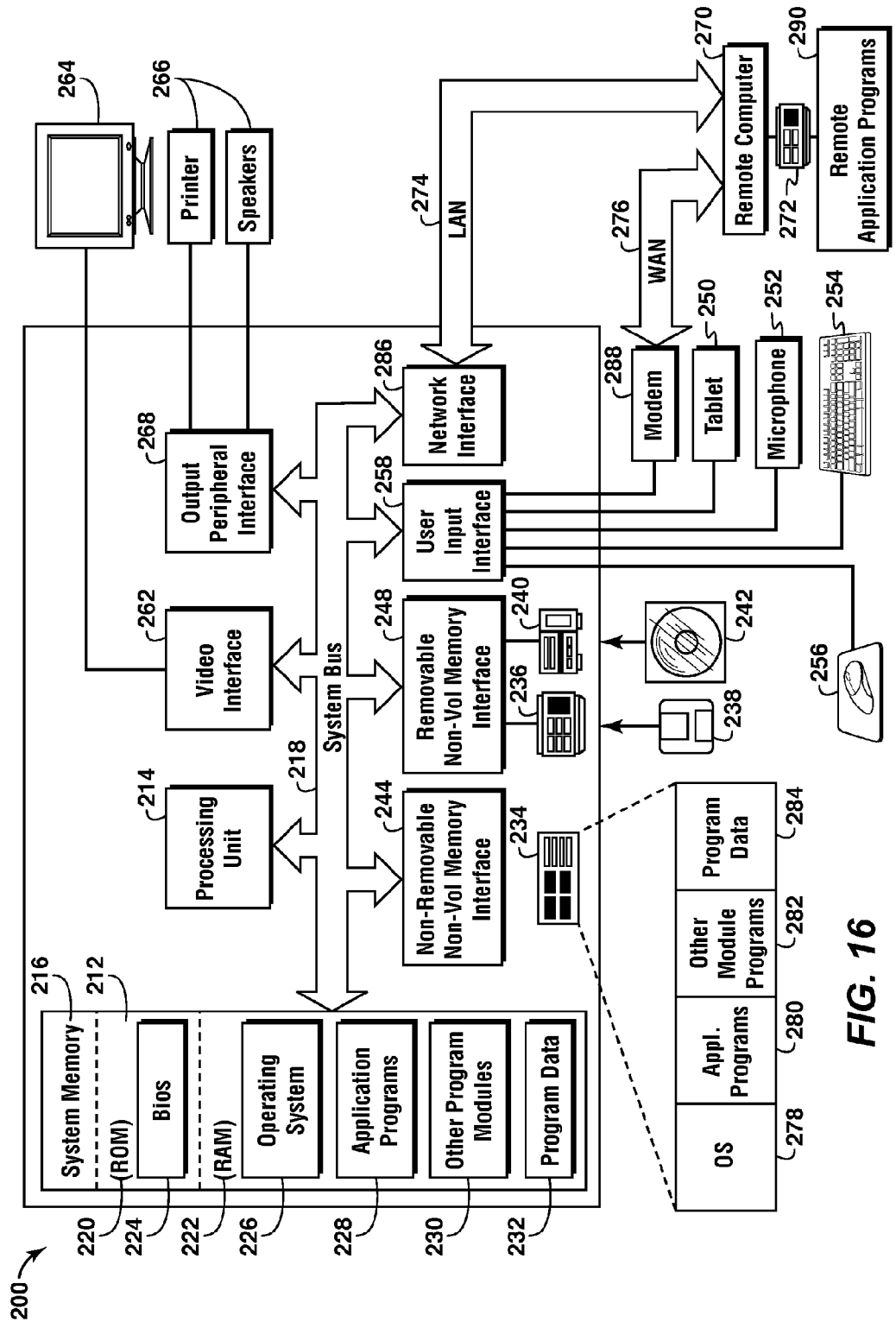
FIG. 16 is a block diagram of a computer system according to aspects of the disclosed methodologies and techniques.

The disclosure has provided various examples of computer systems or portions thereof, any of which may be used to provide an HPR monitoring system and/or an HPR processing system. A more complete illustration of a system for implementing aspects of the disclosed methodologies and techniques is depicted in FIG. 16, it being understood that aspects previously disclosed may be incorporated into part or all of the system in FIG. 16. The system includes a computing device in the form of a computing system 210, which may be a UNIX-based workstation or a commercially available system from Intel, IBM, AMD, Motorola, Cyrix and/or others. Components of the computing system 210 may include, but are not limited to, a processing unit 214, a system memory 216, and a system bus 246 that couples various system components including the system memory to the processing unit 214. The system bus 246 may be any of several types of bus structures including a memory bus or memory controller, a peripheral bus, and a local bus using any of a variety of bus architectures.

Computing system 210 typically includes a variety of computer readable media. Computer readable media may be any available media that may be accessed by the computing system 210 and includes both volatile and nonvolatile media, and removable and non-removable media. By way of example, and not limitation, computer readable media may comprise computer storage media and communication media. Computer storage media includes volatile and nonvolatile, removable and non removable media implemented in any method or technology for storage of information such as computer readable instructions, data structures, program modules or other data.

Computer memory includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may be accessed by the computing system 210.

The system memory 216 includes computer storage media in the form of volatile and/or nonvolatile memory such as read only memory (ROM) 220 and random access memory (RAM) 222. A basic input/output system 224 (BIOS), containing the basic routines that help to transfer information between elements within computing system 210, such as during start-up, is typically stored in ROM 220. RAM 222 typically contains data and/or program modules that are immediately accessible to and/or presently being operated on by processing unit 214. By way of example, and not limitation, FIG. 16 illustrates operating system 226, application programs 230, other program modules 230 and program data 232.

Computing system 210 may also include other removable/non-removable, volatile/nonvolatile computer storage media. By way of example only, FIG. 16 illustrates a hard disk drive 234 that reads from or writes to non-removable, nonvolatile magnetic media, a magnetic disk drive 236 that reads from or writes to a removable, nonvolatile magnetic disk 238, and an optical disk drive 240 that reads from or writes to a removable, nonvolatile optical disk 242 such as a CD ROM or other optical media. Other removable/non-removable, volatile/nonvolatile computer storage media that may be used in the exemplary operating environment include, but are not limited to, magnetic tape cassettes, flash memory cards, digital versatile disks, digital video tape, solid state RAM, solid state ROM, and the like. The hard disk drive 234 is typically connected to the system bus 246 through a non-removable memory interface such as interface 244, and magnetic disk drive 236 and optical disk drive 240 are typically connected to the system bus 246 by a removable memory interface, such as interface 248.

The drives and their associated computer storage media, discussed above and illustrated in FIG. 16, provide storage of computer readable instructions, data structures, program modules and other data for the computing system 210. In FIG. 16, for example, hard disk drive 234 is illustrated as storing operating system 278, application programs 280, other program modules 282 and program data 284. These components may either be the same as or different from operating system 226, application programs 230, other program modules 230, and program data 232. Operating system 278, application programs 280, other program modules 282, and program data 284 are given different numbers hereto illustrates that, at a minimum, they are different copies.

A user may enter commands and information into the computing system 210 through input devices such as a tablet, or electronic digitizer, 250, a microphone 252, a keyboard 254, and pointing device 256, commonly referred to as a mouse, trackball, or touch pad. These and other input devices often may be connected to the processing unit 214 through a user input interface 258 that is coupled to the system bus 218, but may be connected by other interface and bus structures, such as a parallel port, game port or a universal serial bus (USB). Other input devices may include various devices that sense human physiological responses as discussed herein.

A monitor 260 or other type of display device may be also connected to the system bus 218 via an interface, such as a video interface 262. The monitor 260 may be integrated with a touch-screen panel or the like. The monitor and/or touch screen panel may be physically coupled to a housing in which the computing system 210 is incorporated, such as in a tablet-type personal computer. In addition, computers such as the computing system 210 may also include other peripheral output devices such as speakers 264 and printer 266, which may be connected through an output peripheral interface 268 or the like.

Computing system 210 may operate in a networked environment using logical connections to one or more remote computers, such as a remote computing system 270. The remote computing system 270 may be a personal computer, a server, a router, a network PC, a peer device or other common network node, and typically includes many or all of the elements described above relative to the computing system 210, although only a memory storage device 272 has been illustrated in FIG. 16. The logical connections depicted in FIG. 16 include a local area network (LAN) 274 connecting through network interface 286 and a wide area network (WAN) 276 connecting via modem 288, but may also include other networks. Such networking environments are commonplace in offices, enterprise-wide computer networks, intranets and the Internet.

For example, computer system 210 may comprise the source machine from which data is being transferred, and the remote computing system 270 may comprise the destination machine. Note however that source and destination machines need not be connected by a network or any other means, but instead, data may be transferred via any machine-readable media capable of being written by the source platform and read by the destination platform or platforms.

The central processor operating system or systems may reside at a central location or distributed locations (i.e., mirrored or stand-alone). Software programs or modules instruct the operating systems to perform tasks such as, but not limited to, facilitating client requests, system maintenance, security, data storage, data backup, data mining, document/report generation and algorithms. The provided functionality may be embodied directly in hardware, in a software module executed by a processor or in any combination of the two.

Furthermore, software operations may be executed, in part or wholly, by one or more servers or a client's system, via hardware, software module or any combination of the two. A software module (program or executable) may reside in RAM memory, flash memory, ROM memory, EPROM memory, EEPROM memory, registers, hard disk, a removable disk, a CD-ROM, DVD, optical disk or any other form of storage medium known in the art. For example, a storage medium may be coupled to the processor such that the processor may read information from, and write information to, the storage medium. In the alternative, the storage medium may be integral to the processor. The processor and the storage medium may also reside in an application-specific integrated circuit (ASIC). The bus may be an optical or conventional bus operating pursuant to various protocols that are well known in the art. One system that may be used is a Linux workstation configuration with a Linux 64-bit or 32-bit Red Hat Linux WS3 operating system, and an NVIDIA Quadro graphics card. However, the system may operate on a wide variety of hardware.

Figure 17:
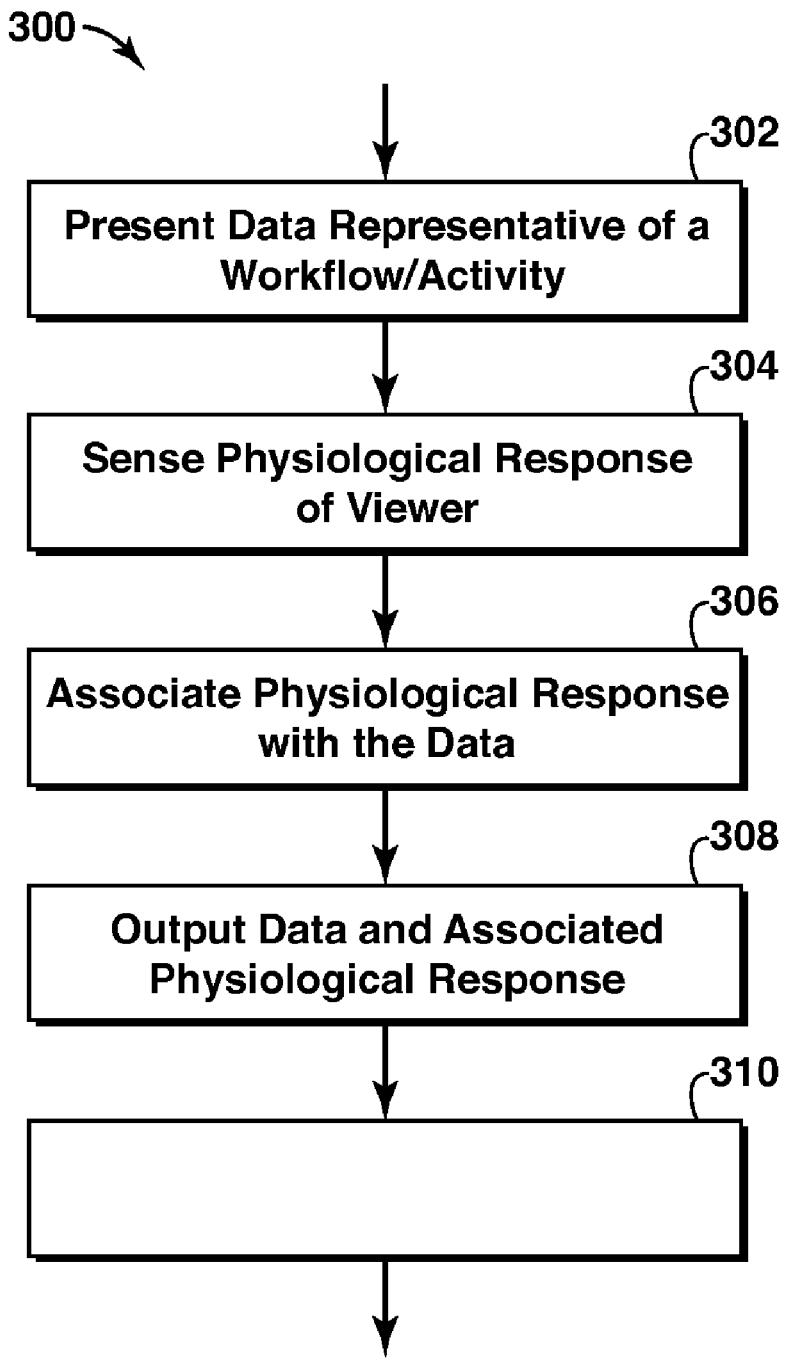
FIG. 17 is a flowchart of a method according to aspects of the disclosed methodologies and techniques.

FIG. 17 is a block diagram of a representation of machine-readable code 300 that may be used with a computing system such as computing system 210. Reference may be made to previously described aspects to more fully explain each block in code 300. At block 302, code is provided for presenting data representative of a workflow or a hydrocarbon management-related activity. At block 304, code is provided for sensing a physiological response of a viewer of the data. At block 306, code is provided for associating the physiological response with the data, and preferably the portion of the data that caused the viewer to experience or effectuate the observed physiological response. At block 308 the data and its associated physiological response are outputted, for example to a display or to a storage device. Code effectuating or executing other features of the disclosed aspects and methodologies may be provided as well. This additional code is represented in FIG. 17 as block 310, and may be placed at any location within code 300 according to computer code programming techniques.

Figure 18:
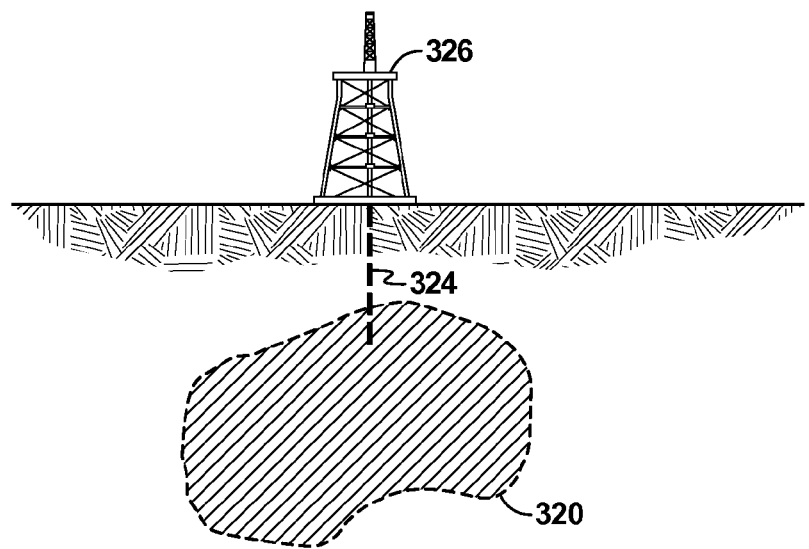
FIG. 18 is a side elevational view of a subsurface region.
Figure 19:
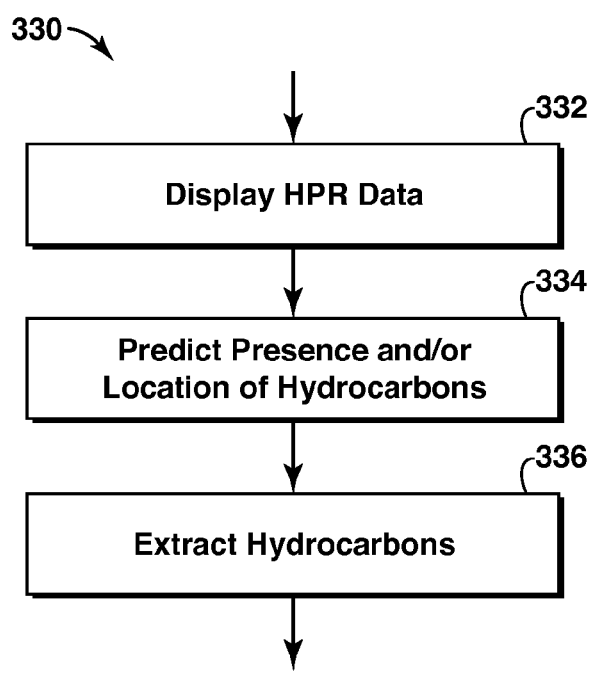
FIG. 19 is a flowchart of a method according to aspects of the disclosed methodologies and techniques.

Aspects disclosed herein may be used to conduct hydrocarbon management activities, such as extracting hydrocarbons from a subsurface region, which is indicated by reference number 320 in FIG. 18. A method 330 of extracting hydrocarbons from subsurface reservoir 320 is shown in FIG. 19. At block 332 HPR data is displayed or provided.

The HPR data may be superimposed on geologic or geophysical data as described and depicted herein. At block 334 the presence and/or location of hydrocarbons in the subsurface region is predicted. At block 336 hydrocarbon extraction is conducted to remove hydrocarbons from the subsurface region, which may be accomplished by drilling a well 334 using oil drilling equipment 336 (FIG. 18). Other hydrocarbon management activities may be performed according to known principles.

The disclosed embodiments and methodologies may be susceptible to various modifications and alternative forms and have been shown only by way of example. The disclosed embodiments and methodologies are not intended to be limited to the particular embodiments disclosed herein, but include all alternatives, modifications, and equivalents falling within the spirit and scope of the appended claims.

What is claimed is:

1. A method for analyzing hydrocarbon-related data, comprising:
    displaying a graphical form of hydrocarbon related data representative of a hydrocarbon entity;
    measuring a physiological response of a viewer of the graphical form of the hydrocarbon related data;
    associating at least one measured physiological response to one or more points within the graphical form of the hydrocarbon related data;
    outputting the hydrocarbon related data; and
    outputting a representation of the measured physiological response of the viewer.

2. The method of claim 1, wherein outputting the representation of the measured physiological response of the viewer comprises displaying the representation of the associated physiological response in a graphical form.

3. The method of claim 2, wherein the representation of the associated physiological response is superimposed upon the graphical form of the hydrocarbon related data.

4. The method of claim 1, wherein the physiological response comprises at least one of brainwave activity, movement of an eye, position of an eye, gaze, muscle movement, body temperature, heart rate, pulmonary performance, and change in tone of voice.

5. The method of claim 1, wherein the physiological response comprises at least one of a rate of use of an input device, and a position of an input device relative to the presented data representative of the hydrocarbon entity.

6. The method of claim 1, wherein outputting the hydrocarbon related data and outputting the representation of the measured physiological response of the viewer comprises storing the data and the associated physiological response in a memory.

7. The method of claim 1, further comprising interpreting the physiological response based on information regarding the viewer.

8. The method of claim 1, wherein outputting the representation of the measured physiological response of the viewer comprises storing the associated measured physiological response in a raw form or a processed form.

9. The method of claim 1, further comprising managing hydrocarbons based at least in part on the associated measured physiological response.

10. A method for analyzing hydrocarbon-related data, comprising:
    displaying a graphical form of hydrocarbon related data representative of a hydrocarbon entity;
    measuring a physiological response of a first viewer and a physiological response of a second viewer of the graphical form of the hydrocarbon related data;
    associating at least one physiological response of the first and second viewers to one or more points within the graphical form of the data; and
    outputting the hydrocarbon related data and a representation of the measured physiological responses of the first and second viewers.

11. An apparatus for analyzing hydrocarbon-related data, comprising:
    one or more sensors for measuring a physiological response of at least one user viewing a graphical form of hydrocarbon related data representative of a hydrocarbon entity to provide one or more measured physiological responses;
    a processor configured to associate the at least one measured physiological response to one or more points within the graphical form of the hydrocarbon related data; and
    an output mechanism for storing a representation of the measured physiological response of the user.

12. The apparatus of claim 11, further comprising a display for viewing the graphical form of the hydrocarbon-related data.

13. The apparatus of claim 11, wherein the one or more sensors includes a device that records brainwave activity of the user or an eye-tracking device that senses one or more eye movements of the user, eye positions of the user, and gazes of the user.

14. The apparatus of claim 13, further comprising a display for viewing the graphical form of the hydrocarbon-related data, and wherein the eye-tracking device is mounted on the display.

15. The apparatus of claim 11, wherein the one or more sensors senses use of an input device as the input device is manipulated by the user, wherein the input device comprises a computer mouse, a computer trackball, or a computer keyboard.

* * * * *